United States Patent [19]
Widlund et al.

[11] 3,996,936
[45] Dec. 14, 1976

[54] BODY FLUID ABSORPTION FIBER FABRIC

[75] Inventors: Leif Urban Roland Widlund, Pixbo; Sven Gunnar Bergdahl, Molnlycke; Kerstin Anna Helena Strandberg, Pixbo, all of Sweden

[73] Assignee: Molnlycke AB, Goteborg, Sweden

[22] Filed: Feb. 4, 1975

[21] Appl. No.: 546,887

[30] Foreign Application Priority Data
Feb. 15, 1974 Sweden .............................. 7402030

[52] U.S. Cl. ............................ 128/287; 128/284
[51] Int. Cl.² ................... A61F 13/20; A61F 13/16
[58] Field of Search ...... 128/284, 287, 288, 290 R, 128/290 P

[56] References Cited
UNITED STATES PATENTS

| | | | |
|---|---|---|---|
| 3,029,817 | 4/1962 | Harwood et al. ............. | 128/296 X |
| 3,595,235 | 7/1971 | Jespersen ......................... | 128/284 |
| 3,683,917 | 8/1972 | Comerford ....................... | 128/287 |
| 3,716,430 | 2/1973 | Croon .............................. | 156/62.4 |
| 3,771,525 | 11/1973 | Chapuis ........................ | 128/290 R |
| 3,805,790 | 4/1974 | Kaczmarzyk .................. | 128/290 R |

*Primary Examiner*—Aldrich F. Medbery
*Attorney, Agent, or Firm*—Young & Thompson

[57] ABSTRACT

Absorption products such as compresses, sanitary napkins, diapers or the like which comprise an absorption body furnished with a covering and an at least substantially moisture-impermeable layer which is provided between said body and said covering on the side of the body facing away from the user. The at least substantially moisture-impervious layer comprises short hydrophobic fibers loosely applied and essentially unbound to one another.

10 Claims, 1 Drawing Figure

U.S. Patent Dec. 14, 1976 3,996,936
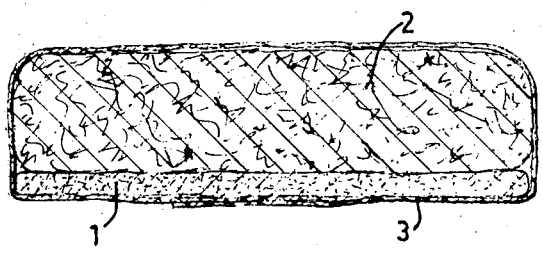

BODY FLUID ABSORPTION FIBER FABRIC

The present invention is related to absorption products such as compresses, sanitary napkins, diapers or the like, which comprise an absorption body furnished with a covering and a layer which is at least substantially moisture-impermeable and which is provided between said body and said covering on the side of the body facing away from the user.

In absorption products of this type various types of attachment arrangements can be employed. This is especially the case with sanitary napkins in which it is, for example, at present common to attach a foam plastic layer or one or more double-sided tape strips or glue strands to the side facing away from the user so that the napkin is held in place through friction or adhesion to the underwear of the user.

The covering normally consists of a non-woven textile material, cellulose material or a meshlike material, while the particularly important absorption body in a product of the type in question normally consists of defibrated hydrophilic cellulose pulp, with or without a number of cellulose layers situated within the body or around the body as a covering. The cellulose layers situated within the body are primarily intended to constitute moisture-distributing members in the cellulose pulp for providing a suitable distribution of moisture within the body, but can also serve as a reinforcement in the body. The cellulose coverings, on the other hand, are the result of manufacturing considerations and are most nearly intended to preserve the outer shape of the absorption body.

There do exist, however, absorption bodies which consist entirely of a plurality of layers of cellulose or of staple fibers.

The at least substantially moisture-impermeable layer is primarily intended to act as a moisture barrier or a barrier layer for preventing the possibility of soaking through, something which is of particular importance in connection with absorption products such as sanitary napkins and diapers. Films of polyethylene, polypropylene, polyvinyl chloride and other plastic materials are known as moisture-impervious liquid barriers or barrier layers in modern absorption products, just as the use of polyethylene and cellulose laminates, hydrophobic cellulose, polymer-coated cellulose and hydrophobic cotton (so-called bandage wadding) for this purpose is also known.

In addition to preventing soaking through, the more or less moisture-impermeable layer serving as a moisture barrier or barrier layer must also meet a large number of at least in part mutually conflicting demands if it is to be suitable in all respects for use in a modern absorption product.

In addition to having an effective moisture-barring ability, so that liquid does not pass through the absorption product during use, this layer should also be air-permeable, so as to provide adequate ventilation of both the absorption product itself and of the area of the body of the user which the product is in contact with during use, so that the occurrence of heat unpleasant for the user and skin moisture are prevented.

If an absorption product of the sanitary napkin or diaper type is to be disposable in a normal sewage system, the at least substantially moisture-impervious layer serving as a barrier layer should also be dispersible in water. In addition the barrier layer in products intended for hospital use, i.e. compresses, bandages and the like, should be sterilizable together with the absorption product in its entirety.

Additionally it is required that the material in the layer in question be soft and rustle-free and that, with reference to the fact that modern absorption products are produced, as a rule, for one-time use, they be inexpensive.

Considering that modern absorption products are produced in automatic machines at a high rate, the material in the at least substantially moisture-impermeable barrier layer should also in a corresponding way be manageable and be attachable at a high rate to the intended products.

The at least substantially moisture-impermeable layers existing to date and the materials used in their production have not, however, been able to meet all of these demands. The most common barrier layer consists of a plastic film. This is indeed moisture-impermeable, soft and moderately inexpensive and possible to manage and attach to the intended absorption product at a high rate, but at the same time the plastic film is not air-permeable and can thus not prevent the occurrence of heat and skin moisture, which is a significant disadvantage. Films of, for example, polyethylene, polypropylene and polyvinyl chloride are also not dispersible in water when flushed down a toilet. On the other hand films of, for example, polyvinyl alcohol or copolymers thereof are indeed soluble in the liquid surplus, but these films suffer instead from the disadvantage of not being wholly moisture-impermeable at the same time as they are regarded as being far too air-tight.

Even if some of the types of polypropylene films are per se heat sterilizable, plastic films have the disadvantage that they are generally not sterilizable in steam and thus cannot be employed in those absorption products which are normally steam sterilized as a matter of routine.

Barrier layers consisting of laminates of a polyethylene film and layers of cellulose or non-woven textile material, like barrier layers of plastic film, suffer from the disadvantages of being air-impermeable and of not being sterilizable in steam or dispersible in water. In addition absorption products furnished with barrier layers of such laminates are somewhat warm and moist to the user.

In contrast to barrier layers consisting of plastic films and of laminates of plastic films and cellulose or of plastic films and non-woven textile material, similar layers consisting of hydrophobic cellulose have the advantages of having at least a certain air-permeability while at the same time being sterilizable in autoclaves, for which reason they are often used in absorption products for hospital purposes. Unfortunately they suffer, as a rule, from the disadvantage of a low degree of moisture repellency and thereby have a relatively poor barrier effect against liquid. It is thus necessary to overlay several layers of hydrophobic cellulose in order to provide a somewhat dependable prevention of soaking through. An at least substantially moisture-impermeable barrier layer formed in this way is therefore expensive because of large material consumption, while simultaneously having the disadvantage of requiring several steps in the production process. In addition dispersibility in water is rather low for barrier layers of hydrophobic cellulose.

Barrier layers of polymer-coated cellulose or polymercoated disintegrable fiber material are known, for example, from Swedish patent Application No. 4888/64 and Swedish Pat. No. 336,270. In spite of the fact that such layers meet several of the previously cited requirements - they are, by way of example, both air-permeable and at least temporarily water impermeable and, in addition, dispersible in water — they suffer from even more important disadvantages. They namely have a limited barrier effect against moisture, for which reason several layers of the same must be employed, with the result that the finished barrier layers are unnecessarily expensive and at the same time are not sterilizable in steam.

Barrier layers product from hydrophobic cotton, socalled bandage wadding, or from other hydrophobic fibers, have been suggested, for example, in the two British Pat. Nos. 608,774 and 1,332,956 and in the two U.S. Pat. Nos. 3,029,817 and 3,771,525. Such barrier layers also meet several of the requirements previously mentioned herein. They are, for example, air-permeable as well as soft and rustle-free. But the number of advantages is wholly outweighed by their disadvantages. Namely they have a rather insignificant moisture-barring effect, at the same time as their dispersibility in water is low as a result of the relatively long fibers contained in them, which, in addition, worsens the managability and requires a production-slowing carding, resulting in an increased cost of production, which in turn makes these barrier layers relatively costly, especially considering their relatively negligible moisture-barring effect.

The comparisons made herein show that there does not, for the present, appear to be or have been suggested any at least substantially moisture-impermeable layers serving as barrier layers in absorption products of the type disclosed in the introduction which meet all of the requirements indicated herein for attainment of a satisfactory barrier layer.

The purpose of the present invention is to provide an arrangement in an absorption product of the type indicated in the introduction which provides an absorption product having at least a substantially moisture-impermeable layer which meets all of the requirements herein imposed on such layers.

According to the invention this purpose is realized quite surprisingly and completely, primarily in that the at least substantially moisture-impervious layer comprises short, hydrophobic fibers, loosely applied to one another and essentially unbound to one another.

The hydrophobic fibers can advantageously consist of moisture-repellent treated fibers, for example cellulose fibers, which offer the advantage that the manufacturer of the absorption product can work with the same starting material for both the hydrophilic absorption body and for the hydrophobic barrier layer.

As a suitable moisture-repellent for the fibers in the barrier layer, alkyl ketendimes in the amount of at least 1.0 percent by weight based on the dry weight of the finished fiber mass are provided according to the invention. For solving the problem of the moisture-barring layer in a desired manner, it has been shown that the at least substantially moisture-impermeable layer should have a weight by unit of volume of between 0.025 and 0.2, but preferably between 0.035 and 0.065 g/cm$^3$.

To achieve the structure suitable for the purpose described herein of the at least substantially moisture-impermeable layer, the mean length of the fibers contained in said structure should be between 0.5 and 20, but preferably between 1 and 10 mm.

To achieve the simplest management and at the same time the least expensive and fastest production of the at least substantially moisture-impermeable layer, it has been found suitable to lay said layer by means of an air current in which the hydrophobic fibers are dispersed. The hydrophobic fibers dispersed in the air current should preferably be freed from a cellulose pulp by means of dry defibration.

The invention will be more closely explained below through embodiments and with reference to the attached drawing, which shows in its FIGURE, a schematically executed cross-section through an absorption product furnished with an embodiment of the invention.

An arrangement according to the present invention comprises the at least substantially moisture-impermeable layer 1, which is provided between the side of an absorption body 2 turned away from the user and a covering 3 enclosing said body in the absorption product shown in the drawing, which can be a compress, a sanitary napkin, a diaper or the like.

The absorption body 2 can, for example, by known means consist of defibrated cellulose pulp having hydrophilic properties suitable for the intended purpose. The covering 3 can, for example, be comprised of a non-woven textile material.

The at least substantially moisture-impermeable layer 1 serving as a barrier layer in the shown absorption product comprises, according to the invention, of short, hydrophobic fibers, loosely applied and essentially unbound to one another, for example, moisture-repellent treated cellulose fibers which are produced through water-proofing natural or regenerated cellulose fibers, having a fiber length of at least 0.5 mm and at most 20 mm, by means of the addition of a moisture-repellent. It has been found that a type of alkyl ketendimes, existing on the market in the form of a 6% aqueous solution under the name of Aquapel 360 XL, is a suitable such repellent.

The repellent should be added to the cellulose fibers in such quantities that at least 1.0% by weight of the repellent based on the dry weight of the repellent-treated fibers remains on the fibers after water extraction and drying. The moisture-repellent can be added to the cellulose fiber mass intended for construction of the barrier layer 1 at a plurality of different stations immediately prior to or at the beginning of a cellulose dehydrator. Suitable stations are the so-called level box before the dehydrator, the socalled dehydrator inlet box, a tubular spray provided especially for this purpose above the endless wire, the warm water spray normally found above the endless wire, a dip roller fixed between two wet presses, in a nip or above a top roller in one of the dehydrator wet presses.

In adding to a diluted pulp, emulsion retention of the water repellent to the cellulose is facilitated if a retention-increasing agent is present. The above-named Aquapel 360 XL contains, in addition to alkyl ketendimes, also cationic starch which acts as a retention agent. As a complement, additional cationic synthetic retention agent can be added, for example of the type of modified polyamide compounds.

It has been found that a suitable combination of good retention and good distribution of the repellent is obtained if it is added together with warm water to the top side of the pulp feed on the endless wire immediately before the suction boxes. For control of distribution and for distinguishing repellent-treated cellulose pulp from common pulp a dye is suitably added together with the repellent.

The repellent-treated cellulose feed is dried by conventional means in the dehydrator and is cut into sheets which are stacked and pressed into bales, or is cut into strips which are rolled up. The bales or rolls can, if necessary, be packed by conventional means and transported to the conversion station.

In an alternative method for repellent-treating cellulose fiber the repellent is added to a fiber suspension which is stored in a vat fitted with a stirrer. The fiber suspension should thereby consist of 0.1% to 3% cellulose fiber in water. After the repellent is evenly distributed in the vat, the suspension is pumped to a dewatering press where dewatering to a dry content of 40 to 50% takes place. The dewatered pulp feed is thereafter disintegrated by means of a shredder and is fed into a hot air current where the fibers are dried by means of a so-called flash drying process. After drying, the fibers are pressed into blocks which are stacked and pressed into bales, which when necessary can also be packed and transported to the conversion station.

In converting the repellent-treated cellulose pulp, which in the form of rolls, sheets or blocks has been transported to the conversion station, the fibers are first freed from one another in the dry state by so-called dry defibration. Several processes for dry defibration are known, for example by means of a hammer mill, a cog shredder, a disc crusher or a disc refiner. Repellent-treated pulp which has been dried by means of a flash drying process can optionally, even prior to final drying, have been disintegrated so closely that the blocks can be disintegrated into free fibers with a very simple shredder.

To attain the at least substantially moisture-impermeable boundary layer 1 the repellent-treated cellulose freed in individual fibers is mixed with an air current, after which the mixture is directed against, for example, a fine-meshed screen. This should be so constructed that the air passes through it while the cellulose fibers remain on the screen where, lying loosely upon and essentially unbound to one another, they form the intended barrier layer 1. If a continuous production of a fiber feed for subsequent dividing into suitable boundary layers 1 is desired, a motion can be imparted to the screen, for example normal to the air current, whereby the fiber feed is built up to the desired thickness during the passage of the screen through the air current. The desired weight of the fiber feed can be determined by regulating the speed of the screen or the fiber concentration in the air current.

If a fiber feed or mat having local variation in thickness is desired, the screen can be furnished with depressions at those locations where a thicker feed or mat is desired. The thickness can then be fine-adjusted by brushing away excess material from the top side of the mat. A feed or mat having local variations in thickness can be divided into barrier layers 1 having stronger barrier effects within the thicker sections.

An irregular form of the barrier layer 1 can also easily be effected without the occurrence of unnecessary waste. Using the known barrier layer material, on the other hand, always results in waste of considerable magnitude.

The invention is not limited to the embodiment described above and shown in the drawing, but can instead be modified in multifarious ways within the scope of the claims.

What we claim is:

1. Absorption products such as compresses, sanitary napkins, diapers or the like which comprise an absorption body furnished with a covering and an at least substantially moisture-impermeable layer which is provided between said body and said covering on the side of the body facing away from the user, characterized in that the at least substantially moisture-impervious layer comprises short hydrophobic fibers loosely applied and essentially unbound to one another.

2. The products of claim 1, characterized in that the hydrophobic fibers consist of moisture-repellent treated fibers.

3. The products of claim 2, characterized in that the repellent-treated fibers are cellulose fibers.

4. The products of claim 2, characterized in that the repellent is of the type alkyl ketendimes in the amount of at least 1.0% by weight based on the dry weight of the finished cellulose pulp.

5. The products of claim 1, characterized in that the at least substantially moisture-impermeable layer has a weight by unit of volume of between 0.025 and 0.2 g/cm$^3$.

6. The products of claim 1, characterized in that the mean fiber length is between 0.5 and 20 mm.

7. The products of claim 1, characterized in that the at least substantially moisture-impermeable layer is laid by means of an air current in which the hydrophobic fibers have been dispersed.

8. The products of claim 7, characterized in that the hydrophobic fibers dispersed in the air current are freed from a cellulose pulp by means of dry defibration.

9. The products of claim 5, characterized in that said weight is between 0.035 and 0.065 g/cm$^3$.

10. The products of claim 6, characterized in that said mean fiber length is between 1 and 10 mm.

* * * * *